(12) United States Patent
Fulkerson (10) Patent No.: US 8,475,399 B2
(45) Date of Patent: Jul. 2, 2013

(54) METHODS AND SYSTEMS FOR MEASURING AND VERIFYING ADDITIVES FOR USE IN A DIALYSIS MACHINE

(75) Inventor: Barry Neil Fulkerson, Longmont, CO (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 49 days.

(21) Appl. No.: 12/713,447

(22) Filed: Feb. 26, 2010

(65) Prior Publication Data

US 2011/0054378 A1    Mar. 3, 2011

Related U.S. Application Data (60) Provisional application No. 61/155,548, filed on Feb. 26, 2009.

(51) Int. Cl.
*A61M 37/00* (2006.01)

(52) U.S. Cl.
USPC .................. 604/5.01; 604/5.04; 604/6.09

(58) Field of Classification Search
USPC .................. 604/5.01, 6.06, 6.09, 6.11, 6.16
See application file for complete search history.

(56) References Cited

U.S. PATENT DOCUMENTS

| | | |
|---|---|---|
| 2,328,381 A | 8/1943 | Jaffe |
| 3,388,803 A | 6/1968 | Scott |
| 3,746,175 A | 7/1973 | Markley |
| 3,884,808 A | 5/1975 | Scott |
| 3,902,490 A | 9/1975 | Jacobsen et al. |
| 3,989,622 A | 11/1976 | Marantz et al. |
| 3,994,799 A | 11/1976 | Yao et al. |
| 4,000,072 A | 12/1976 | Sato et al. |
| 4,071,444 A | 1/1978 | Ash et al. |
| 4,094,775 A | 6/1978 | Mueller |
| 4,118,314 A | 10/1978 | Yoshida |
| 4,209,392 A | 6/1980 | Wallace |
| 4,212,738 A | 7/1980 | Henne |
| 4,247,393 A | 1/1981 | Wallace |
| 4,267,040 A | 5/1981 | Schal |
| 4,269,708 A | 5/1981 | Bonomini et al. |
| 4,326,955 A | 4/1982 | Babb et al. |
| 4,348,283 A | 9/1982 | Ash |
| 4,354,562 A * | 10/1982 | Newman ................ 177/210 EM |
| 4,368,737 A | 1/1983 | Ash |
| 4,387,777 A | 6/1983 | Ash |
| 4,402,694 A | 9/1983 | Ash et al. |
| 4,403,984 A | 9/1983 | Ash et al. |
| 4,413,988 A | 11/1983 | Handt et al. |
| 4,443,333 A | 4/1984 | Mahurkar |
| 4,469,593 A | 9/1984 | Ishihara et al. |
| 4,498,902 A | 2/1985 | Ash et al. |
| 4,559,039 A | 12/1985 | Ash et al. |

(Continued)

*Primary Examiner* — Leslie Deak
*Assistant Examiner* — Sara Sass
(74) *Attorney, Agent, or Firm* — Novel IP (57) ABSTRACT

The present application discloses a portable dialysis system for conducting a dialysis treatment. The portable dialysis system has a controller unit that includes a display, a scale, a bar code reader, and a memory storing a plurality of programmatic instructions. Upon execution, the instructions generate a first graphical user interface, a second graphical user interface, and a third graphical user interface for presentation on the display. The first graphical user interface displays each additive required for use in the dialysis treatment. The second graphical user interface prompts a user to submit additives to scanning using the bar code scanner. The third graphical user interface prompts a user to submit additives to measurement using the scale.

20 Claims, 7 Drawing Sheets

U.S. PATENT DOCUMENTS

| | | |
|---|---|---|
| 4,563,170 A | 1/1986 | Aigner |
| 4,581,141 A | 4/1986 | Ash |
| 4,661,246 A | 4/1987 | Ash |
| 4,765,907 A | 8/1988 | Scott |
| 4,777,953 A | 10/1988 | Ash et al. |
| 4,806,247 A | 2/1989 | Schoendorfer et al. |
| 4,828,543 A | 5/1989 | Weiss et al. |
| 4,854,322 A | 8/1989 | Ash et al. |
| 4,897,189 A | 1/1990 | Greenwood et al. |
| 4,914,819 A | 4/1990 | Ash |
| 4,950,395 A | 8/1990 | Richalley |
| 4,968,422 A | 11/1990 | Runge et al. |
| 4,995,268 A | 2/1991 | Ash et al. |
| 4,997,570 A | 3/1991 | Polaschegg |
| 5,002,054 A | 3/1991 | Ash et al. |
| 5,032,261 A | 7/1991 | Pyper |
| 5,074,368 A * | 12/1991 | Bullivant .................. 177/50 |
| 5,100,554 A | 3/1992 | Polaschegg |
| 5,114,580 A | 5/1992 | Ahmad et al. |
| 5,147,613 A | 9/1992 | Heilmann et al. |
| 5,198,335 A | 3/1993 | Sekikawa et al. |
| 5,211,643 A | 5/1993 | Reinhardt et al. |
| 5,230,341 A | 7/1993 | Polaschegg |
| 5,277,820 A | 1/1994 | Ash |
| 5,284,470 A | 2/1994 | Beltz |
| 5,284,559 A | 2/1994 | Lim et al. |
| 5,295,505 A | 3/1994 | Polaschegg et al. |
| 5,304,349 A | 4/1994 | Polaschegg |
| 5,308,315 A | 5/1994 | Khuri et al. |
| 5,322,519 A | 6/1994 | Ash |
| 5,360,445 A | 11/1994 | Goldowsky |
| 5,385,005 A | 1/1995 | Ash |
| D355,816 S | 2/1995 | Ash |
| 5,391,143 A | 2/1995 | Kensey |
| 5,405,315 A | 4/1995 | Khuri et al. |
| 5,405,320 A | 4/1995 | Twardowski et al. |
| 5,415,532 A | 5/1995 | Loughnane et al. |
| 5,445,630 A | 8/1995 | Richmond |
| 5,476,444 A | 12/1995 | Keeling et al. |
| D370,531 S | 6/1996 | Ash et al. |
| 5,536,412 A | 7/1996 | Ash |
| 5,540,265 A | 7/1996 | Polaschegg et al. |
| 5,545,131 A | 8/1996 | Davankov |
| 5,577,891 A | 11/1996 | Loughnane et al. |
| 5,580,460 A | 12/1996 | Polaschegg |
| 5,614,677 A | 3/1997 | Wamsiedler et al. |
| 5,616,305 A | 4/1997 | Mathieu |
| 5,624,551 A | 4/1997 | Baumann et al. |
| 5,632,897 A | 5/1997 | Mathieu |
| 5,698,083 A | 12/1997 | Glass |
| 5,711,883 A | 1/1998 | Folden et al. |
| 5,713,850 A | 2/1998 | Heilmann et al. |
| 5,725,773 A | 3/1998 | Polaschegg |
| 5,725,776 A | 3/1998 | Kenley et al. |
| 5,794,669 A | 8/1998 | Polaschegg et al. |
| 5,858,186 A | 1/1999 | Glass |
| 5,876,419 A | 3/1999 | Carpenter et al. |
| 5,902,336 A | 5/1999 | Mishkin |
| 5,906,978 A | 5/1999 | Ash |
| 5,919,369 A | 7/1999 | Ash |
| 5,944,684 A | 8/1999 | Roberts et al. |
| 5,947,953 A | 9/1999 | Ash et al. |
| 5,980,481 A | 11/1999 | Gorsuch |
| 5,984,891 A | 11/1999 | Keilman et al. |
| 6,042,561 A | 3/2000 | Ash et al. |
| 6,117,100 A | 9/2000 | Powers et al. |
| 6,117,122 A | 9/2000 | Din et al. |
| 6,156,007 A | 12/2000 | Ash |
| 6,168,578 B1 | 1/2001 | Diamond |
| 6,190,349 B1 | 2/2001 | Ash et al. |
| 6,196,922 B1 | 3/2001 | Hantschk et al. |
| 6,196,992 B1 | 3/2001 | Keilman et al. |
| 6,217,540 B1 | 4/2001 | Yazawa et al. |
| 6,254,567 B1 | 7/2001 | Treu et al. |
| 6,264,680 B1 | 7/2001 | Ash |
| 6,287,516 B1 | 9/2001 | Matson et al. |
| 6,303,036 B1 | 10/2001 | Collins et al. |
| 6,325,774 B1 | 12/2001 | Bene et al. |
| 6,332,985 B1 | 12/2001 | Sherman et al. |
| 6,348,162 B1 | 2/2002 | Ash |
| 6,406,631 B1 | 6/2002 | Collins et al. |
| 6,409,699 B1 | 6/2002 | Ash |
| 6,471,872 B2 | 10/2002 | Kitaevich et al. |
| 6,491,673 B1 | 12/2002 | Palumbo et al. |
| 6,497,675 B1 | 12/2002 | Davankov |
| 6,551,513 B2 | 4/2003 | Nikaido et al. |
| 6,554,789 B1 | 4/2003 | Brugger et al. |
| 6,561,997 B1 | 5/2003 | Funke et al. |
| 6,572,576 B2 | 6/2003 | Brugger et al. |
| 6,572,641 B2 | 6/2003 | Brugger et al. |
| 6,579,253 B1 | 6/2003 | Burbank et al. |
| 6,579,460 B1 | 6/2003 | Willis et al. |
| 6,582,385 B2 | 6/2003 | Burbank et al. |
| 6,589,482 B1 | 7/2003 | Burbank et al. |
| 6,595,943 B1 | 7/2003 | Burbank |
| 6,610,036 B2 | 8/2003 | Branch et al. |
| 6,623,470 B2 | 9/2003 | Munis et al. |
| 6,627,164 B1 | 9/2003 | Wong |
| 6,632,192 B2 | 10/2003 | Gorsuch et al. |
| 6,638,477 B1 | 10/2003 | Treu et al. |
| 6,638,478 B1 | 10/2003 | Treu et al. |
| 6,649,063 B2 | 11/2003 | Brugger et al. |
| 6,673,314 B1 | 1/2004 | Burbank et al. |
| 6,685,664 B2 | 2/2004 | Levin et al. |
| 6,702,561 B2 | 3/2004 | Stillig et al. |
| 6,706,007 B2 | 3/2004 | Gelfand et al. |
| 6,730,266 B2 | 5/2004 | Matson et al. |
| 6,743,193 B2 | 6/2004 | Brugger et al. |
| 6,758,975 B2 | 7/2004 | Peabody et al. |
| 6,776,912 B2 | 8/2004 | Baurmeister |
| 6,796,955 B2 | 9/2004 | O'Mahony et al. |
| 6,818,196 B2 | 11/2004 | Wong |
| 6,830,553 B1 | 12/2004 | Burbank et al. |
| 6,841,172 B1 | 1/2005 | Ash |
| 6,843,779 B1 | 1/2005 | Andrysiak et al. |
| 6,852,090 B2 | 2/2005 | Burbank et al. |
| 6,872,346 B2 | 3/2005 | Stillig |
| 6,878,283 B2 | 4/2005 | Thompson |
| 6,890,315 B1 | 5/2005 | Levin et al. |
| 6,955,655 B2 | 10/2005 | Burbank et al. |
| 6,958,049 B1 | 10/2005 | Ash |
| 6,960,179 B2 | 11/2005 | Gura |
| 6,960,328 B2 | 11/2005 | Bortun et al. |
| 6,979,309 B2 | 12/2005 | Burbank et al. |
| 7,004,924 B1 | 2/2006 | Brugger et al. |
| 7,033,498 B2 | 4/2006 | Wong |
| 7,040,142 B2 | 5/2006 | Burbank |
| 7,087,033 B2 | 8/2006 | Brugger et al. |
| 7,101,519 B2 | 9/2006 | Wong |
| 7,112,273 B2 | 9/2006 | Weigel et al. |
| 7,115,095 B2 | 10/2006 | Eigler et al. |
| 7,135,156 B2 | 11/2006 | Hai et al. |
| 7,144,386 B2 | 12/2006 | Korkor et al. |
| 7,147,613 B2 | 12/2006 | Burbank et al. |
| 7,169,303 B2 | 1/2007 | Sullivan et al. |
| 7,175,809 B2 | 2/2007 | Gelfand et al. |
| 7,214,312 B2 | 5/2007 | Brugger et al. |
| 7,226,538 B2 | 6/2007 | Brugger et al. |
| 7,241,272 B2 | 7/2007 | Karoor et al. |
| 7,252,767 B2 | 8/2007 | Bortun et al. |
| 7,267,658 B2 | 9/2007 | Treu et al. |
| 7,273,465 B2 | 9/2007 | Ash |
| 7,276,042 B2 | 10/2007 | Polaschegg et al. |
| 7,300,413 B2 | 11/2007 | Burbank et al. |
| 7,309,323 B2 | 12/2007 | Gura et al. |
| 7,337,674 B2 | 3/2008 | Burbank et al. |
| 7,338,460 B2 | 3/2008 | Burbank et al. |
| 7,347,849 B2 | 3/2008 | Brugger et al. |
| 7,351,218 B2 | 4/2008 | Bene |
| 7,597,677 B2 | 10/2009 | Gura et al. |
| 7,645,253 B2 | 1/2010 | Gura et al. |
| 2002/0068364 A1 | 6/2002 | Arai et al. |
| 2002/0085951 A1 | 7/2002 | Gelfand et al. |
| 2002/0112609 A1 | 8/2002 | Wong |
| 2003/0048185 A1* | 3/2003 | Citrenbaum et al. ......... 340/540 |
| 2003/0236482 A1 | 12/2003 | Gorsuch et al. |
| 2005/0086008 A1* | 4/2005 | DiGianfilippo et al. ........ 702/19 |

| | | | | | |
|---|---|---|---|---|---|
| 2006/0064053 A1* | 3/2006 | Bollish et al. .................. 604/31 | 2008/0051689 A1 | 2/2008 | Gura et al. |
| 2006/0122552 A1 | 6/2006 | O'Mahony | 2008/0058696 A1 | 3/2008 | Gura et al. |
| 2006/0241543 A1 | 10/2006 | Gura | 2008/0217245 A1 | 9/2008 | Rambod et al. |
| 2007/0060786 A1 | 3/2007 | Gura et al. | 2010/0022936 A1 | 1/2010 | Gura et al. |
| 2007/0161113 A1 | 7/2007 | Ash | 2010/0094193 A1 | 4/2010 | Gura et al. |
| 2007/0179425 A1 | 8/2007 | Gura et al. | 2010/0209300 A1* | 8/2010 | Dirac et al. ................ 422/82.05 |
| 2008/0006570 A1 | 1/2008 | Gura et al. | | | |
| 2008/0021366 A1 | 1/2008 | Gura et al. | | | |
| 2008/0041136 A1 | 2/2008 | Kopelman et al. | * cited by examiner | | |

METHODS AND SYSTEMS FOR MEASURING AND VERIFYING ADDITIVES FOR USE IN A DIALYSIS MACHINE

CROSS-REFERENCE

The present invention relies on U.S. Patent Provisional No. 61/155,548, filed on Feb. 26, 2009, for priority. The present invention is also related to a) U.S. patent application Ser. No. 12/575,450, filed on Oct. 7, 2009, b) U.S. patent application Ser. No. 12/575,449, filed on Oct. 7, 2009, c) U.S. patent application Ser. No. 12/355,102, filed on Jan. 16, 2009, d) U.S. patent application Ser. No. 12/355,128, filed on Jan. 16, 2009, e) U.S. patent application Ser. No. 12/351,969, filed on Jan. 12, 2009, f) U.S. patent application Ser. No. 12/324,924, filed on Nov. 28, 2008, g) U.S. patent application Ser. No. 12/210,080, filed on Sep. 12, 2008, h) U.S. patent application Ser. No. 12/238,055, filed on Sep. 25, 2008, i) U.S. patent application Ser. No. 12/237,914, filed on Sep. 25, 2008, j) U.S. patent application Ser. No. 12/249,090, filed on Oct. 10, 2008, k) U.S. patent application Ser. No. 12/245,397, filed on Oct. 3, 2008, l) U.S. patent application Ser. No. 12/610,032, filed on Oct. 30, 2009, m) U.S. patent application Ser. No. 12/610,100, filed on Oct. 30, 2009, and n) U.S. patent application Ser. No. 12/705,054, filed on Feb. 12, 2010. All of the specifications and drawings of the aforementioned applications are herein incorporated by reference in their entirety.

FIELD

The present invention relates generally to the field of blood purification systems and methods. More specifically, the present invention relates to a portable system for conducting hemofiltration and hemodialysis, and methods for measuring and verifying additives in the same.

BACKGROUND

Blood purification systems form the final line of treatment in the case of conditions such as renal dysfunction. Blood purification systems, which are used for conducting hemodialysis, hemodiafiltration or hemofiltration, involve extracorporeal circulation of blood through an exchanger having a semi permeable membrane. Such systems further include a hydraulic system for circulating blood and a hydraulic system for circulating replacement fluid or dialysate comprising the main electrolytes of the blood in concentrations close to those in the blood of a healthy subject.

Conventional blood purification systems are, however, quite bulky in size and difficult to operate. Hemodialysis procedures using standard equipment also tend to be costly, in addition to being cumbersome, and require the patient to be bound to a dialysis center for long durations. Conventional systems are also less reliable because of the necessity of using a myriad of tubes comprising the fluid circuits of the purification systems, thus increasing the risks of leakage and breakage.

Portable or mobile blood purification systems have been developed for home use. However, because such systems are intended to be used and operated by patients or individuals who do not have medical training, it is essential that these systems be sufficiently user-friendly to be understandable without the need for medical training and, furthermore, to monitor, constrain, or otherwise manage user actions, and user interactions with the system, in order to prevent errors, or notify if an error is suspected.

Accordingly there is need in the art for an extracorporeal blood processing system that offers reasonable portability to the patient while at the same time conducting hemodialysis as well as hemofiltration procedures safely and effectively. Further, such a portable dialysis system should also be capable of accurately measuring and verifying any prescription additives to the patient along with the dialysate fluid. It is also desirable that such a portable dialysis system should be conducive to using disposable components and further, should have built-in functionality to check the integrity and authenticity of the disposables employed in the system as well as that of the prescription additives being dispensed by the system.

SUMMARY

The present application discloses a portable dialysis system for conducting a dialysis treatment, wherein said portable dialysis system comprises: a display; a scale; a bar code reader; a memory storing a plurality of programmatic instructions wherein, upon execution, said instructions generate: a first graphical user interface for presentation on said display, wherein said first graphical user interface displays each additive required for use in the dialysis treatment; a second graphical user interface for presentation on said display, wherein said second graphical user interface prompts a user of said system to submit a plurality of additives to scanning using said bar code scanner; and a third graphical user interface for presentation on said display, wherein said third graphical user interface prompts a user of said system to submit a plurality of additives to measurement using said scale.

Optionally, the scale is a digital scale. The digital scale further comprises a plurality of hall sensors. The controller is configured to physically attach to a base unit, wherein said base unit comprises a reservoir and said digital scale. The bar code scanner provides a visual indication of a successful read. The memory further comprises a table associating a plurality of additive names with a plurality of bar codes. The memory further comprises a table associating a plurality of additives with a plurality of weight values. The first graphical user interface displays a visual representation of the additive packaging. The third graphical user interface only prompts the user of said system to submit a plurality of additives to measurement using said scale if a bar code of an additive is not recognized or available.

The present application also discloses a portable dialysis system for conducting a dialysis treatment, wherein said portable dialysis system comprises: a display; a scale having a plurality of magnets and corresponding sensors; an electronic reader; a memory storing a plurality of programmatic instructions wherein, upon execution, said instructions generate: a first graphical user interface for presentation on said display, wherein said first graphical user interface prompts a user of said system to submit a plurality of additives to scanning using said bar code scanner; and a second graphical user interface for presentation on said display, wherein said second graphical user interface prompts a user of said system to submit a plurality of additives to measurement using said scale.

Optionally, upon execution, the instructions further generate a third graphical user interface for presentation on said display, wherein said third graphical user interface displays each additive required for use in the dialysis treatment. The scale is a digital scale and generates data representative of a weight of an object placed on said digital scale. The digital scale further comprises at least three flexures. Each of said flexures comprises a magnet and a hall sensor. The controller is configured to physically attach to a base unit, wherein said base unit comprises a reservoir and said digital scale. The memory further comprises a table associating a plurality of additive names with a plurality of bar codes. The memory further comprises a table associating a plurality of additives with a plurality of weight values. The second graphical user interface only prompts the user of said system to submit a plurality of additives to measurement using said scale if a bar code of an additive is not recognized. The second graphical user interface only prompts the user of said system to submit a plurality of additives to measurement using said scale if a bar code for an additive is not available.

BRIEF DESCRIPTION

These and other features and advantages of the present invention will be appreciated, as they become better understood by reference to the following detailed description when considered in connection with the accompanying drawings, wherein.

DETAILED DESCRIPTION

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
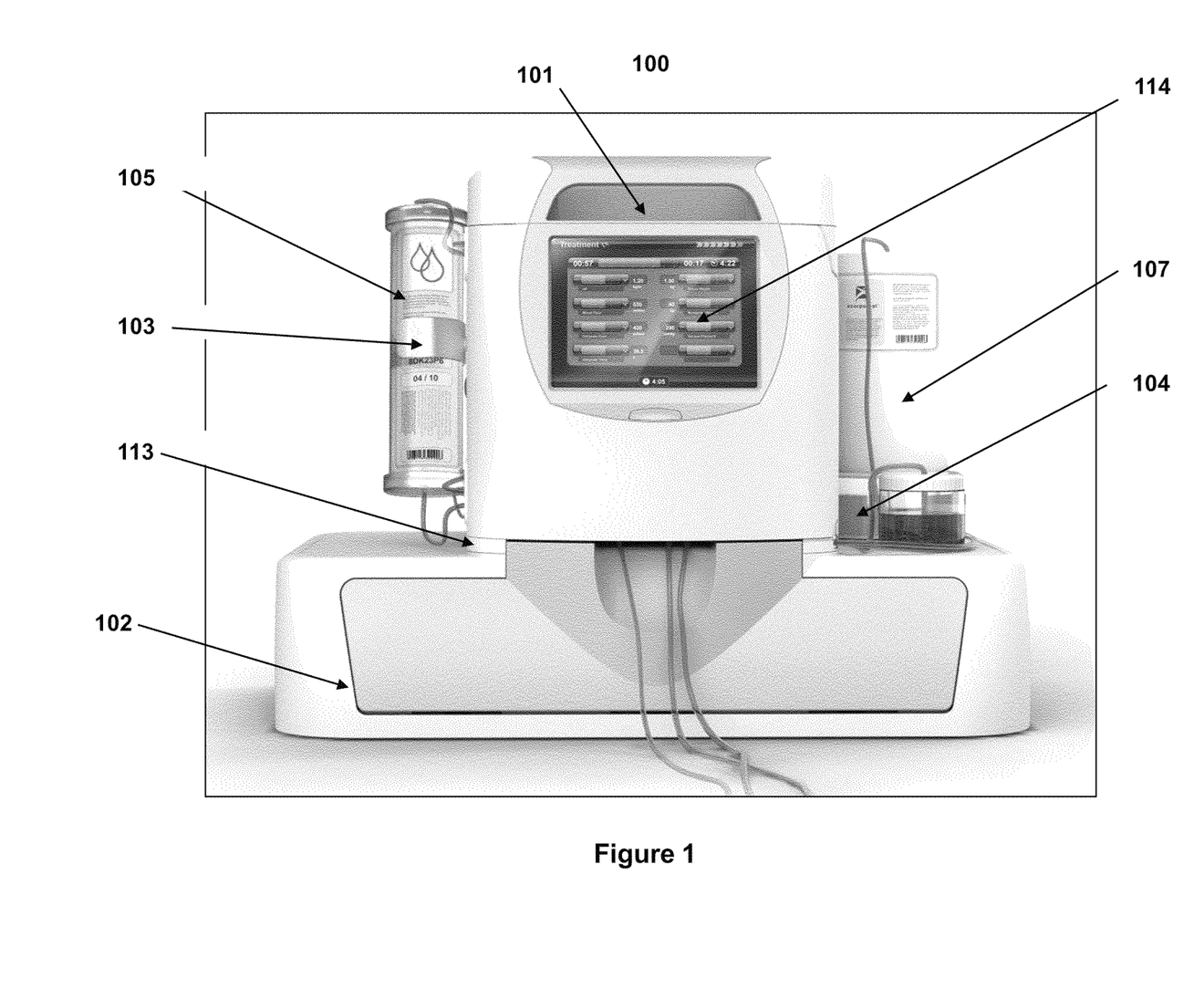
FIG. 1 illustrates the front view of one embodiment a dialysis system of the present invention.

The present invention is directed toward a dialysis unit that is modular and portable, with the capability of accurately measuring and verifying additives to the patient, along with dialysate fluid. FIG. 1 illustrates the front view of one embodiment the portable dialysis system of the present invention. Referring to FIG. 1, the portable dialysis system 100 comprises a controller unit 101 that is detachably affixed to a base 102. The base 102 comprises a reservoir for fluid storage. The device 100 is provided with a clasp 103 on one side, which can be used to detachably affix a hemofilter 105. The device 100 is also provided with a base receiver 104 on the other side to which a sorbent cartridge 107 can be detachably affixed.

The dialysis system of the present invention has disposable components provided separately. This allows the device to be separated into multiple units for installation, service, and travel, with each subunit being easily handled, packaged and carried. The two component design further provides flexibility in product growth. For example, if improvements are made to the controller unit or, separately, to the reservoir (such as reducing fluid volume or a change in volume scale measurement), an existing customer need only upgrade one of the two component parts, not both. Similarly, if only one of the two components breaks down, a customer requires only the broken part to be repaired or to be replaced, instead of replacing the whole system.

Structurally, the dialysis system 100 has a latching mechanism 113 between the two major components of the system— the controller unit 101 and the base reservoir unit 102. The presence and use of the latching mechanism 113 reduces the likelihood of an accidental disconnection between the two components, as compared to the case when the two components are simply stacked atop each other without a latch. Further, since the latch mechanism is designed to ensure solid alignment between the top and bottom components, it facilitates the use of electronic components—such as exposed electronic connectors on the bottom of the top unit and top of the bottom unit, which automatically come into contact and complete a power circuit when the units are properly aligned. This permits the use of a single power supply and simple connection/disconnection. In one embodiment, the latch mechanism uses no tools and is simply achieved using a male/female mating connections present on the top component and bottom component.

The front of the top unit 101 is provided with a graphical user interface (GUI) 114 for the system 100. To facilitate the use of the portable dialysis system 100 in a home setting, the GUI is designed to be user friendly and simple. The GUI 114 uses a touch screen panel and makes an optimum use of colors to highlight the key features. In one embodiment, the touch screen allows multiple user input configurations, provides multiple language capability, and can be readily seen at night. The GUI further includes a feature for the automatic closing, opening, and locking of the latching mechanism 113 during operation. In other embodiments, the GUI 114 comprises feathertouch buttons and/or a key pad or keyboard.

Figure 2:
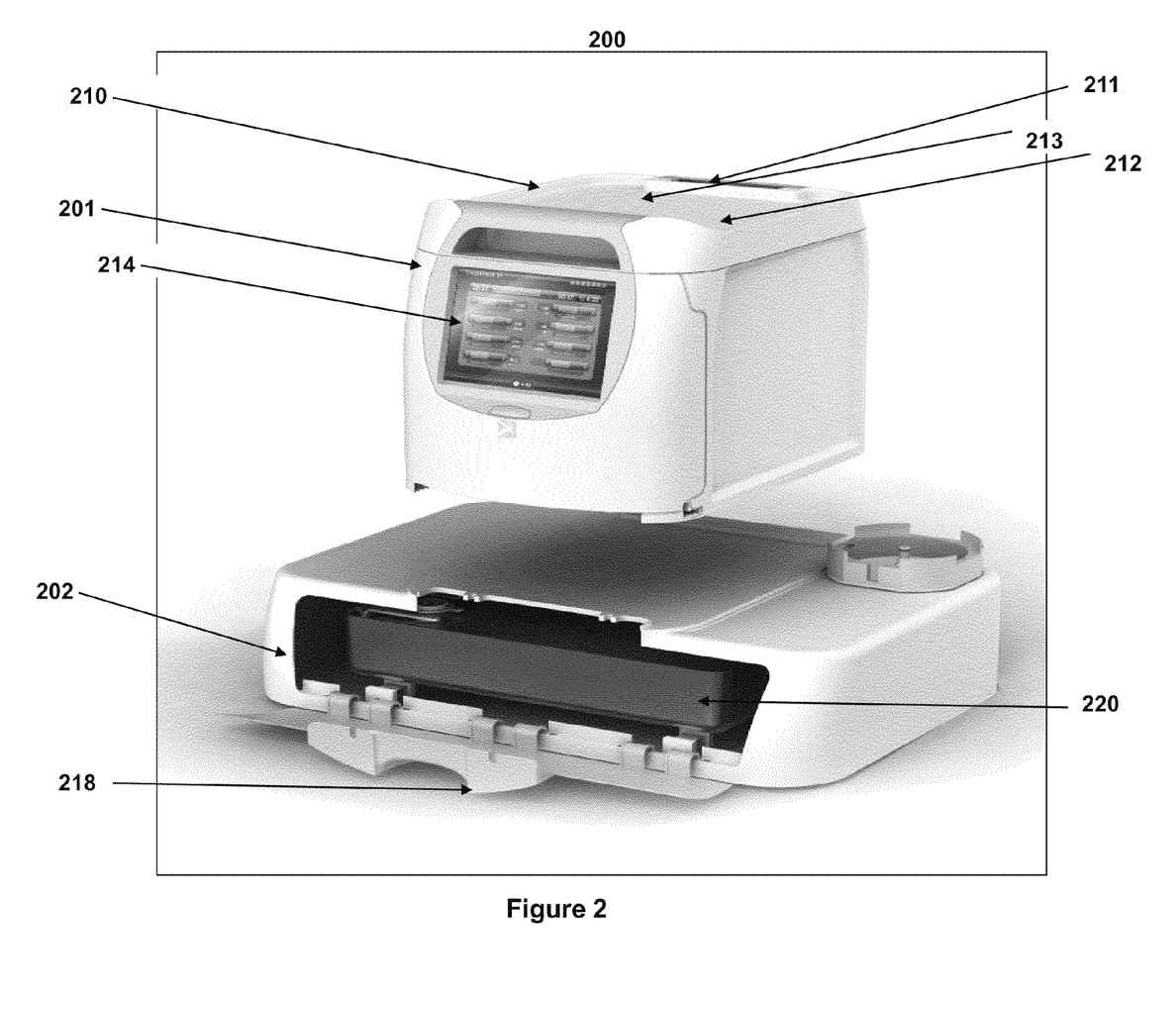
FIG. 2 illustrates another view of one embodiment of a dialysis system of the present invention.

FIG. 2 provides another view of the portable dialysis system of the present invention. Referring to FIG. 2, atop the controller unit 201 are handles 211 which in one embodiment, are directly connected to the internal structure of the system, and can be used to reposition the system in a manner that is safe, particularly when the instrument is in operation with a large quantity of fluid.

In one embodiment, the top surface of the controller unit 201 is designed to be substantially flat and is provided with side-walls 210 such that it forms a useable shelf or tray 212. In one embodiment, the usable shelf 212 is equipped with a digital scale 213 that can be used for accurate measurement of any additives, such as sodium chloride, dextrose, etc or any drugs that are to be added to the dialysate fluid. Thus, prior to starting the dialysis process using the portable dialysis system 200, the user collects all the packets of additives that have been provided, prescribed, or are otherwise required, and places them one by one on the scale 213 on the portable dialysis system 200. The additive packets are each weighed individually. The measured weight is compared against an expected weight. If there are any discrepancies, an alarm is initiated and, via the GUI 114, the user is informed of the discrepancy and asked to make sure the right additive packet, with the right amount, is being weighed. According, weight discrepancies help determine if a wrong packet has been selected.

The bottom component 202 of the system 200 is provided with a door 218, which when pulled open provides access to the fluid reservoir. In one embodiment, the digital scale 213 is integrated in the bottom component 202, such that the scale tray 220 slides out when the door 218 is pulled open. A button may be provided for opening and closing the scale tray.

Figure 3A:
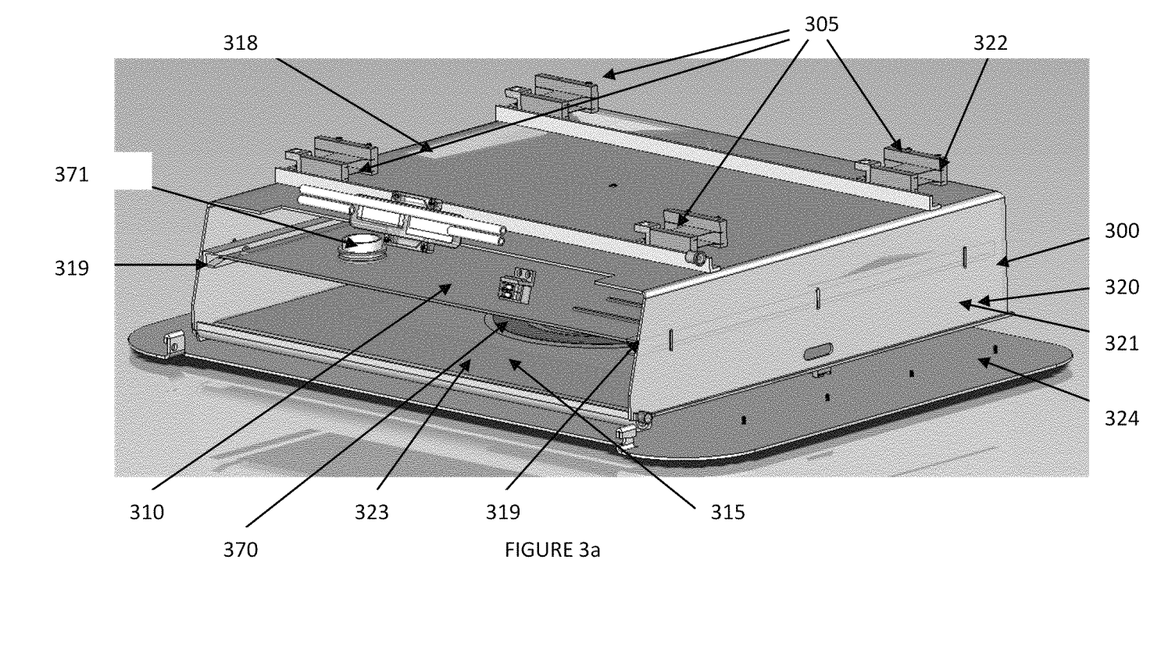
FIG. 3a is a side perspective view of a reservoir with an integrated scale.
Figure 3B:
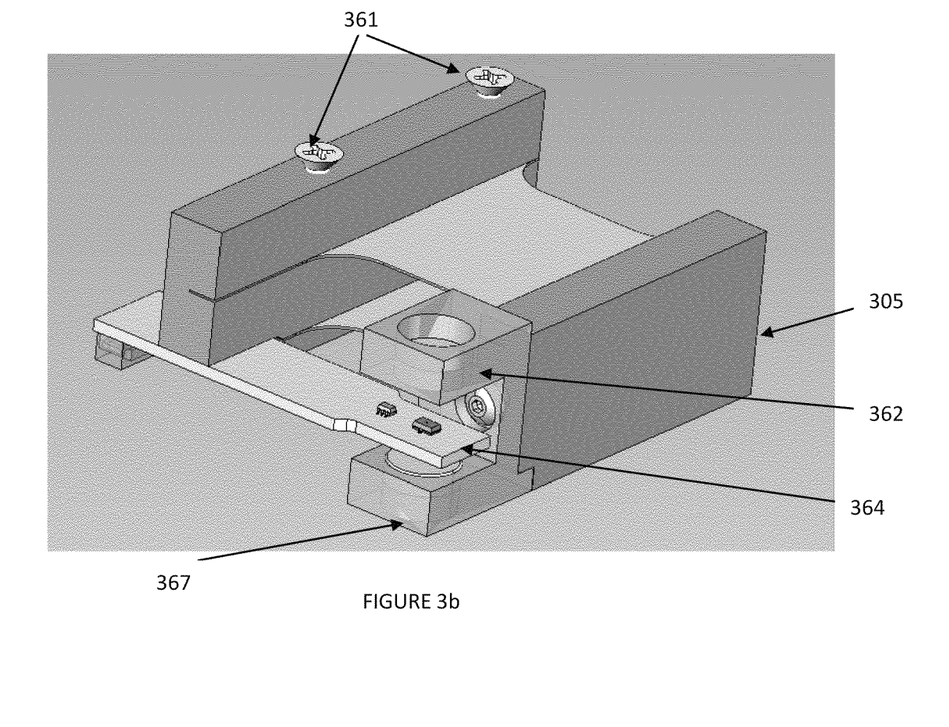
FIG. 3b is a side perspective view of a flexure assembly.

FIGS. 3a and 3b illustrate an exemplary digital scale system that can be used with the portable dialysis system of the present invention. As described earlier, the scale 213 can be integrated on the shelf atop the controller unit 201, inside the bottom unit of the portable dialysis system, or in any other location that provides a sufficiently flat, unobstructed area for users to measure additives.

In one embodiment, the scale is integrally formed with a reservoir unit which is configured to removably attach to the bottom of the controller unit 201. Referring to FIG. 3a, the internal structure 300 of the scale plus reservoir system is shown. A metallic internal frame 320 comprises two sides 321, a back 322, and open faced front 323, and a base 324. The internal structure or frame is shown without the external housing, as depicted as element 102 in FIG. 1. A scale 318 is integrated into the reservoir internal structure 300. The bottom surface 315 of the scale 318 comprises a metal surface or pan that, together with the rest of the scale 318, is suspended from the external reservoir housing (shown as 102 in FIG. 1) by four flexures 305. Below the bottom surface 315 of the scale is preferably situated a heating pad, such as a square, rectangular, circular, or other shaped surface capable of incurring a temperature increase and conducting the increased temperature, as heat, to surface 315. A conductivity coil 370, capable of exerting a field and using changes in that field to measure conductivity, is integrated into base surface 315. Accordingly, when a reservoir bag (not shown) is placed on bottom surface 315, it can be heated by a heating pad and, because it is in contact with coil 370, its conductivity can be monitored.

In one embodiment, the scale base 315 is detachable from the frame 320 and capable of being ejected outward from the unit 102 in order to accept additive package(s) from a user and capable of returning to its internal position in order to initiate the weighing of the additive packages.

The internal surfaces of the sides 321 comprise a plurality of rails, elongated members, or protrusions 319 that serve to secure, hold, encase or attach to a disposable reservoir bag mounting surface, such as a plastic sheet, 310 to which a reservoir bag can be attached. Specifically, a reservoir bag positioned on surface 315 can have an outlet attached to conduit 371 integrated into sheet 310. Mounted in each of the four corners of the scale surface 318 are flexures 305 with each one comprising a hall sensor and magnet.

Referring to FIG. 3b, the flexure 305 comprises a plurality of attachment points 361 where the flexure is secured to the external reservoir housing. The flexure further comprises magnetic bodies 362, such as two magnets, and a hall sensor 364. The base 367 of the flexure 305 is attached to the top surface 315 of scale 318. As the scale 318 displaces due to the application of a weight load (e.g. when a plurality of additive packages have been placed thereon, thereby pressing on surface 315 and pulling scale 318 downward), the flexure 305, which is connected to the scale at one end and the external housing at another end, will flex and the magnet 362, mounted on the one end of the flexure 305, will track that change by virtue of changes to the magnetic field generated by the magnetic body 362. The hall sensor 364 detects changes in the magnetic field strength. One of ordinary skill in the art would understand how to translate this sensed magnetic field change into a measure of the applied weight load.

In another embodiment, three flexures, rather than four, are used and configured in a triangular pattern. It should be appreciated that three or more flexures could be used to implement the scale as described herein. In another embodiment, the scale base comprises a portion of the exterior of the unit (100 from FIG. 1), with the scale base physically attached to the flexures, which may be mounted on railings connected to the unit 100 exterior. One of ordinary skill in the art would appreciate that other methods of implementing a scale could be applied and such other methods would be fall within the scope of the present invention.

Referring back to FIG. 2, the measurement readings taken by the digital scale are displayed via graphical user interfaces shown on display 214. In one embodiment, the controller unit 201 is programmed in accordance with the user's prescription. This can be done by means of an initial setup in which the user places all the packets of prescription additives one by one on the scale tray. The measurements made by the digital scale are recorded and stored in an internal memory. The controller 201 thus has access to the data regarding names and prescribed weights of the additives. Therefore, when a packet of any prescription additive is placed on the scale for measurement prior to starting the dialysis process, the controller compares the measured weight with the prescribed weight stored in an internal memory. In case of any discrepancy between the measured weight and the correct or prescribed weight, the controller 201 directs the GUI to display an alarm or directs an audio generation unit to generate an auditory alarm. Therefore, such an alarm may be visual, such as a flashing error message on the GUI screen, and may also be accompanied by an audible alarm. Alternatively, a user is not permitted to continue the dialysis set up process.

Figure 4:
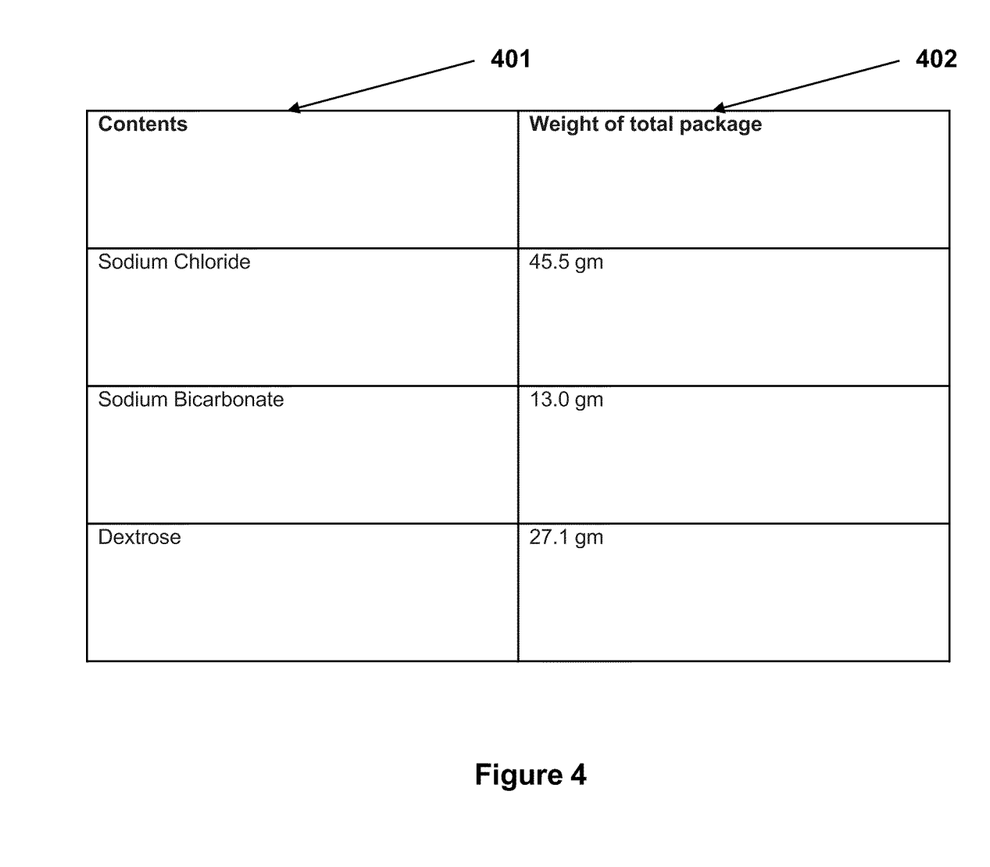
FIG. 4 illustrates an exemplary table of data that may be stored in the internal memory of the dialysis system.

FIG. 4 illustrates an exemplary table of data for prescription additives that may be stored as a file, flat file, or table in the internal memory of the portable dialysis system. Column 401 describes the packet contents and column 402 shows the corresponding weight. As can be seen from column 402, the weight difference between the different packages is several grams, which can be read by a digital scale. In one embodiment, the digital scale of the present invention is designed with a weight resolution of the order of 0.1 gm, which, given the weight of additives, provides a greater than 5 times resolution advantage and, more preferably, 10 times resolution advantage. This resolution is sufficient to differentiate between the typically used additives.

Further, the structure of the digital scale is designed such that the weighing process is not affected by the manner in which a user places the packets of prescription additives on the scale. This is because the structure of the scale in the present invention comprises multiple weight-sensitive members at multiple suspension points. In one embodiment for example, the scale comprises three sensors on a three point suspension. The total weight is computed by the scale system as the SUM of that measured by all the sensors. The advantage of using this computing scheme is that the packet weight need not be evenly distributed on the scale platform. Thus, even if the packets are placed on the scale tray slightly off to one side, flat or scrunched, it would not affect the accuracy of weight measurement made by the scale. That is, a user is not constrained in the manner in which he places the packets on the scale.

It should further be appreciated that the sensor weight can be determined using any calculation method known in the art. In one embodiment, a processor in data communication with the scale 318 receives data readings from said scale 318 and determines a weight as follows:

$$Sensor\_Weight(i) = K1(i) * ADC(reading) + K0(i)$$

$$Bag\_Weight = (Sensor\_Weight(0) + Sensor\_Weight(1) + Sensor\_Weight(2) + Sensor\_Weight(3))/4$$

Figure 5:
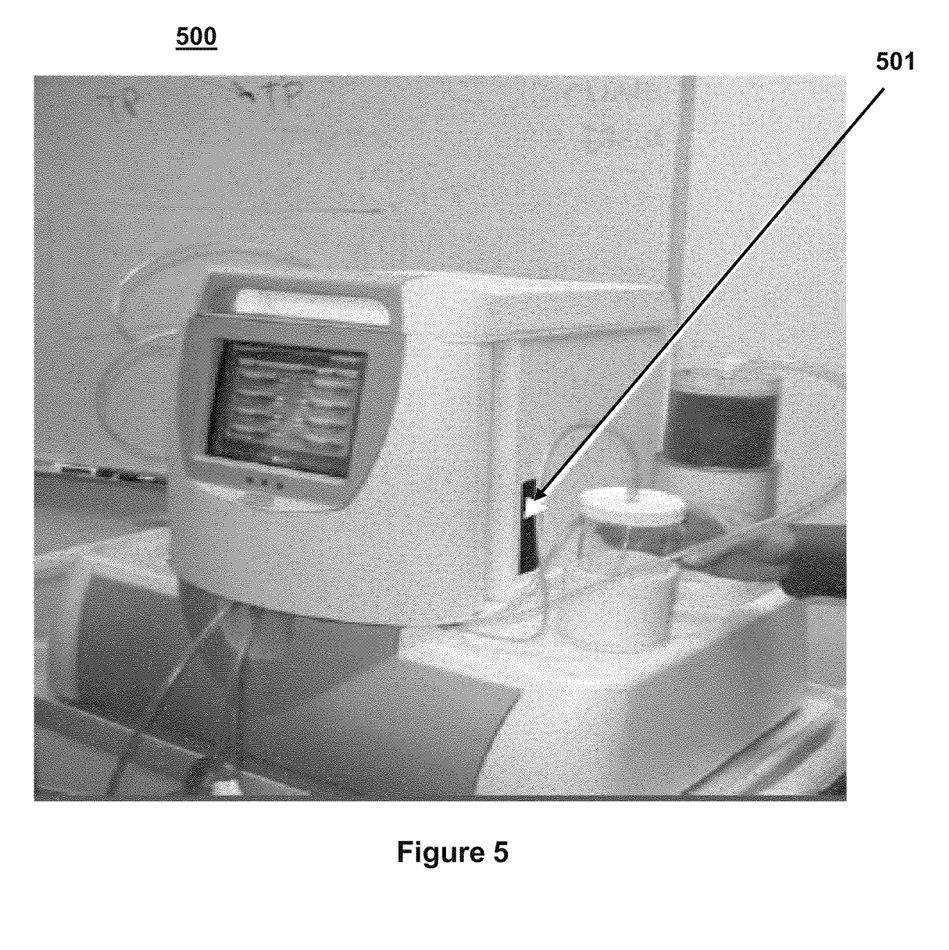
FIG. 5 illustrates a bar code or tag reader as used with the portable dialysis system of the present invention.

Another structural feature of the portable dialysis system of the present invention, according to one embodiment is shown in FIG. 5. The portable dialysis system 500 has an exposed reader 501, such as a bar code reader or RFID tag reader, which can be used to read codes or tags on the packets of prescribed additives. For initial setup, a user would preferably swipe all of the codes/tags on the packets of prescription additives by the reader 501. The user can be assisted through an initial GUI message which prompts the user to swipe each packet of prescription additive past the reader 501. Upon doing so, the reader obtains identifying information about the additive and transmits that identifying information to an internal table stored in memory. After this initial setup, whenever a prescription additive is to be added to the dialysate prior to starting dialysis, the identifying information of the concerned packet (read by the reader 501) is compared to the identifying information for that additive already stored in the internal table during initial setup. This helps to verify that the correct additives have been selected for use with the dialysate and helps rule out any spurious additives. The contents of the internal table can be generated either by manual input of data regarding the identity and weight of the additives or by remote access to a prescription that details the identity and amount of the additives.

In one embodiment, the GUI of the present invention is generated by a plurality of programmatic instructions stored and executed by a processor resident in the controller unit. One set of programmatic instructions is designed to walk a user through a process for verifying the identity and amount of additives to be used. A first GUI screen prompts a user to expose a bar code on an additive bag to the bar code reader. One of ordinary skill in the art would appreciate that this identifying mechanism can be a bar code, RFID tag, or other electronic tag, and the reader can be a bar code reader, RFID tag reader, or other electronic tag reader. The reader reads the coded information, processes it using a processor, and transmits the processed information to a memory. The memory has a programmatic routine that translates the processed information into an identity of an additive. In one embodiment, the translation is facilitated by a table that matches various identifiers to specific additive names. This table can be manually inputted prior to the procedure or downloaded from a server via a wired or wireless connection to the controller.

Once the additive identity is obtained, the GUI communicates the identity of the additive to the user and instructs the user to place the additive on the scale. The digital scale weighs the additive and communicates the measured weight to a second table. The second table maps the additive identity with the expected weight. This second table may be manually inputted prior to the procedure or downloaded from a server via a wired or wireless connection to the controller. If the additive identity and measured weight match, the user is instructed to open the packet and pour the contents into the appropriate location. This process is repeated for all the additives. In one embodiment, a user is not permitted to continue the process if there is a discrepancy between the identity of the packet and its weight or if the coded identity of the packet cannot be read or is unknown. Thus, the system of present invention provides a one step or two-step verification mechanism: a) using the digital scale by itself or b) using the digital scale in combination with the bar code or tag reader, which ensures that the user has, in his or her possession, all of the required additives and that the correct additives are being used and not counterfeit or unsuitable.

Figure 6:
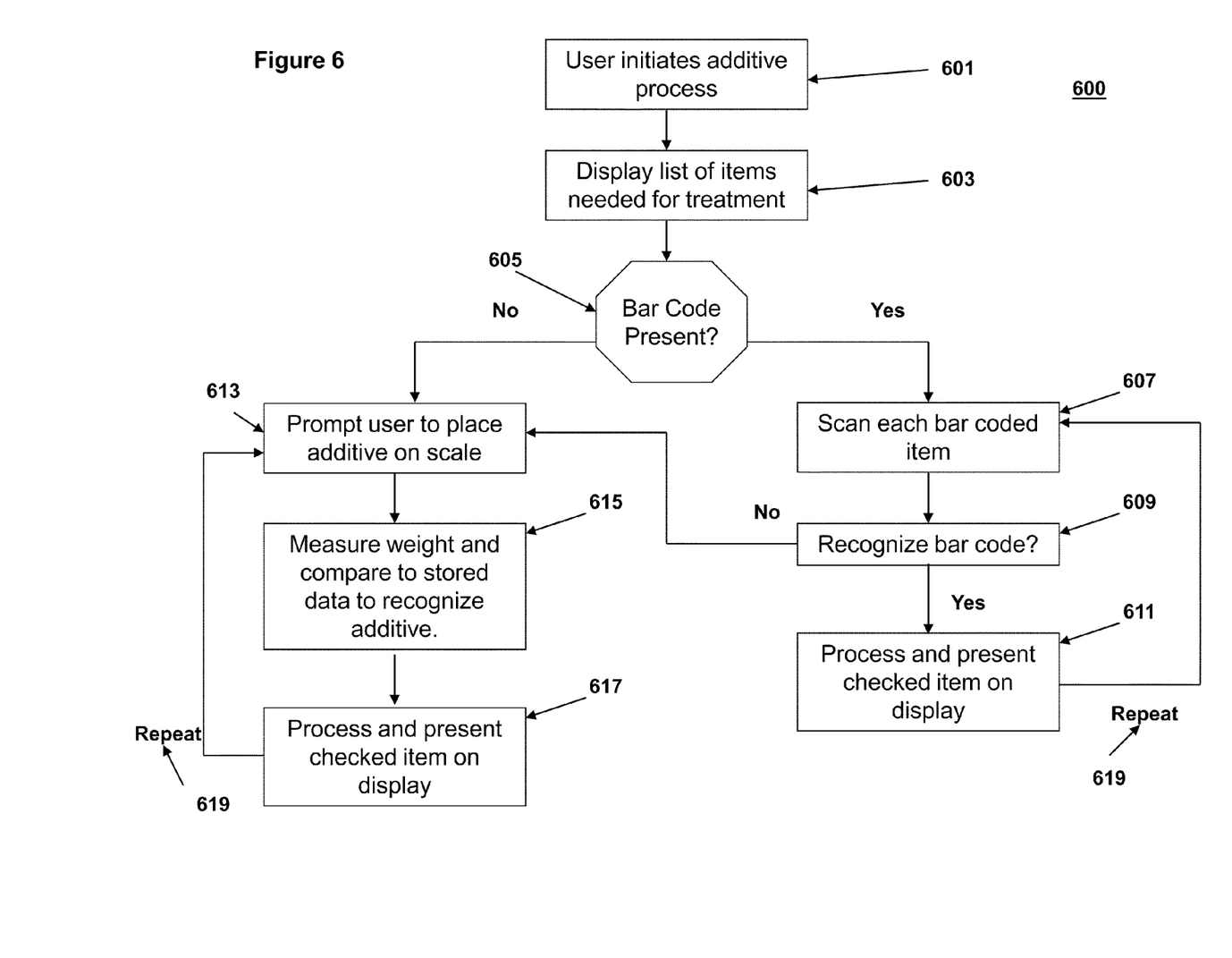
FIG. 6 is a flowchart demonstrating an exemplary process for directing a user through the additive addition process.

Referring to FIG. 6, a flowchart showing another process 600 for initiating a dialysis treatment. In one embodiment, the controller unit 201 comprises at least one processor and memory storing a plurality of programmatic instructions. When executed by the processor, the programmatic instructions generate a plurality of graphical user interfaces, displayed on the controller display 214, which directs a user through a series of actions designed to reliably acquire and measure the additives required for use in a dialysis treatment. A first graphical user interface is generated through which a user can prompt the system to initiative the additive accounting process 601. The initial prompt can be through a specific icon for initiating the process or can occur as part of a larger system setup.

A second graphical user interface is then generated which displays in text or graphical form the additives required, preferably including a visual image of the actual additive package to permit a user to visually compare the additive required with the product the user has on-hand. The user is then prompted 605 to indicate whether he wishes to verify the additive using a bar code scan or by weight. If the user indicates he wishes to use the bar code scan, through, for example, pressing an icon, a third graphical user interface is generated 607 prompting the user to pass the first additive past the bar code scanner. The user then passes an additive, preferably in any order, past the bar code scanner, registering a read. It should be appreciated that the bar code scanner can comprise a light, such as a red light, which changes color, such as to green, upon a successful reading. If the system successfully reads the bar code 609, it processes 611 the code by checking the code against a table stored in memory. The table stored in memory associates bar codes with specific additives. Once a specific additive is identified, the second graphical user interface, as described above, is updated with a check mark or highlight to indicate which additive has been successfully scanned and the user is instructed to set the additive aside. This process is repeated for all additives. In one embodiment, once all additives are highlighted or checked, the system automatically proceeds to the next step in the dialysis set up or initialization process. In another embodiment, once all additives are highlighted or checked, the system presents a graphical user interface informing the user that all additives have been registered, after which a user causes the system to manually proceed to the next step in the dialysis set up or initialization process. It should be appreciated that, while the term bar code is used, any electronic tagging or labeling system can be used.

If, for any scanning step 609 the bar code is not recognized, the additives do not have bar codes, or the user prefers to verify additives using weighing, as opposed to scanning, a graphical user interface is presented to the user prompting 613 the user to place a first additive on the scale. The scale measures the additive package weight 615 and compares the measured weight to a table of weight values associated with specific additives in order to recognize the additive. Once recognized, the second graphical user interface, as described above, is updated 617 with a check mark or highlight to indicate which additive has been successfully scanned and the user is instructed to set the additive aside. This process is repeated 619 for all additives. In one embodiment, once all additives are highlighted or checked, the system automatically proceeds to the next step in the dialysis set up or initialization process. In another embodiment, once all additives are highlighted or checked, the system presents a graphical user interface informing the user that all additives have been registered, after which a user causes the system to manually proceed to the next step in the dialysis set up or initialization process. It should be appreciated that, while the term bar code is used, any electronic tagging or labeling system can be used.

If the additive is not recognized, the user is informed that the additive is not part of the treatment process and is prompted to weigh a proper additive. In another embodiment, if the user fails to scan or weigh a recognized additive, the user is not permitted to continue the initialization or set up process.

One of ordinary skill in the art would appreciate that although the aforementioned verification procedure has been described for prescription additives, the same procedure may also be extended to the disposable components used with the dialysis system, such as sorbent cartridges and other disposables.

It should further be appreciated that the process of scanning and weighing the additives can be integrated and automated. As discussed above, a user can be prompted to initiate the additive weighing process and a display of items needed for treatment may be displayed. A user places an additive on a scale which has a bar code reader proximate to or integrated therein. In one embodiment, the user is prompted to place the additive in a specific position or configuration to ensure the bar code can be properly read. Upon placing the additive on the scale having an integrated or combined bar code reader, the bar code reader scans the additive, attempts to recognize the bar code, and, if recognized, processes the item by checking or highlighting the identified additive on the display. If the bar code reader fails to identify the additive, if the system requires an additional, supplemental check, or if the system wishes to obtain or otherwise record weight information, the scale measures the weight and attempts to recognize the additive against stored values. If identified, the system processes the item by checking or highlighting the identified additive on the display. The scale measurement and bar code reader can therefore occur without having to move the additive from one location or position to another.

It should further be appreciated that the additives can be inserted into a holding container, chute, cylinder, box, bucket, or staging area that will automatically drop, place, or otherwise position each additive into the appropriate position on a scale/bar code reader. Accordingly, the user can place all additives into a single container, activate the system, and have each additive sequentially positioned on the scale and identified automatically. A user may be prompted to remove each additive after each additive is recognized or maybe prompted to allow all additives to be processed first.

It should further be appreciated that the additive can be added to the system automatically after identification, manually after identification, and either before or after the hemofilter and/or sorbent cartridge is installed.

In one embodiment, the top or bottom unit of the portable dialysis system also preferably has electronic interfaces, such as Ethernet connections or USB ports, to enable a direct connection to a network, thereby facilitating remote prescription verification, compliance vigilance, and other remote servicing operations. The USB ports also permit direct connection to accessory products such as blood pressure monitors or hematocrit/saturation monitors. The interfaces are electronically isolated, thereby ensuring patient safety regardless of the quality of the interfacing device.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof.

I claim:

1. A portable dialysis system for conducting a dialysis treatment, wherein said portable dialysis system comprises:
   a. first housing having a display and having a dialyzer, plurality of pumps and fluid flow paths for conducting said dialysis treatment;
   b. a second housing having water reservoir, a scale and a bar code reader, wherein the first housing is adapted to physically attach to, and sit on top of, the second housing and wherein a fluid flow path places water in said water reservoir in fluid communication with at least one of the fluid flow paths in the first housing; and
   c. a memory, located in the first housing, for storing a plurality of programmatic instructions wherein, upon execution, said instructions generate:
      i. a first graphical user interface for presentation on said display, wherein said first graphical user interface displays each additive required for use in the dialysis treatment;
      ii. a second graphical user interface for presentation on said display, wherein said second graphical user interface prompts a user of said system to submit a plurality of additives to scanning using said bar code scanner; and
      iii. a third graphical user interface for presentation on said display, wherein said third graphical user interface prompts a user of said system to submit a plurality of additives to measurement using said scale.

2. The dialysis system of claim 1 wherein said scale is a digital scale.

3. The dialysis system of claim 2 wherein said digital scale further comprises a plurality of hall sensors.

4. The dialysis system of claim 2 wherein said second housing a reservoir and said digital scale.

5. The dialysis system of claim 1 wherein the bar code scanner provides a visual indication of a successful read.

6. The dialysis system of claim 1 wherein the memory further comprises a table associating a plurality of additive names with a plurality of bar codes.

7. The dialysis system of claim 1 wherein the memory further comprises a table associating a plurality of additives with a plurality of weight values.

8. The dialysis system of claim 1 wherein the first graphical user interface displays a visual representation of the additive packaging.

9. The dialysis system of claim 1 wherein said third graphical user interface only prompts the user of said system to submit a plurality of additives to measurement using said scale if a bar code of an additive is not recognized.

10. The dialysis system of claim 1 wherein said third graphical user interface only prompts the user of said system to submit a plurality of additives to measurement using said scale if a bar code for an additive is not available.

11. A portable dialysis system for conducting a dialysis treatment, wherein said portable dialysis system comprises:
   a. first housing having a display and having a dialyzer, a plurality of pumps and fluid flow paths for conducting said dialysis treatment;
   b. a second housing having a scale comprising a water reservoir, a plurality of magnets and a bar code reader, wherein the first housing is adapted to physically attach to the second housing and wherein a fluid flow path places water in said water reservoir in fluid communication with at least one of the fluid flow paths in the first housing; and
c. a memory, located in the first housing, for storing a plurality of programmatic instructions wherein, upon execution, said instructions generate:
   i. a first graphical user interface for presentation on said display, wherein said first graphical user interface prompts a user of said system to submit a plurality of additives to scanning using said bar code scanner; and
   ii. a second graphical user interface for presentation on said display, wherein said second graphical user interface prompts a user of said system to submit a plurality of additives to measurement using said scale.

12. The portable dialysis system of claim 11 wherein, upon execution, said instructions further generate a third graphical user interface for presentation on said display, wherein said third graphical user interface displays each additive required for use in the dialysis treatment.

13. The dialysis system of claim 11 wherein said scale is a digital scale and wherein said digital scale generates data representative of a weight of an object placed on said digital scale.

14. The dialysis system of claim 13 wherein said digital scale further comprises at least three flexures.

15. The dialysis system of claim 14 wherein each of said flexures comprises a magnet and a corresponding hall sensor.

16. The dialysis system of claim 13 wherein said second housing a reservoir and said digital scale.

17. The dialysis system of claim 11 wherein the memory further comprises a table associating a plurality of additive names with a plurality of bar codes.

18. The dialysis system of claim 11 wherein the memory further comprises a table associating a plurality of additives with a plurality of weight values.

19. The dialysis system of claim 11 wherein said second graphical user interface only prompts the user of said system to submit a plurality of additives to measurement using said scale if a bar code of an additive is not recognized.

20. The dialysis system of claim 11 wherein said second graphical user interface only prompts the user of said system to submit a plurality of additives to measurement using said scale if a bar code for an additive is not available.

* * * * *